US 8,187,331 B2

(12) United States Patent
Strohkirch, Jr. et al.

(10) Patent No.: US 8,187,331 B2
(45) Date of Patent: May 29, 2012

(54) EXPANDABLE VERTEBRAL IMPLANT AND METHODS OF USE

(75) Inventors: Terrance Strohkirch, Jr., Memphis, TN (US); Harold Sparr Taylor, Memphis, TN (US); Michael S Veldman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1152 days.

(21) Appl. No.: 11/412,441

(22) Filed: Apr. 27, 2006

(65) Prior Publication Data

US 2007/0270964 A1    Nov. 22, 2007

(51) Int. Cl.
*A61F 2/44* (2006.01)
(52) U.S. Cl. ............... 623/17.16; 623/17.15; 623/17.11
(58) Field of Classification Search .... 623/17.11–17.16; 254/243, 133 A
See application file for complete search history.

(56) References Cited

U.S. PATENT DOCUMENTS

| | | | |
|---|---|---|---|
| 1,611,765 A * | 12/1926 | Meyer | 248/354.1 |
| 2,548,844 A * | 4/1951 | Myers | 254/98 |
| 4,553,273 A | 11/1985 | Wu | |
| 4,554,914 A | 11/1985 | Kapp et al. | |
| 4,657,550 A | 4/1987 | Daher | |
| 4,820,305 A | 4/1989 | Harms et al. | |
| 4,932,975 A | 6/1990 | Main et al. | |
| 5,026,373 A | 6/1991 | Ray et al. | |
| 5,062,850 A | 11/1991 | MacMillan et al. | |
| 5,236,460 A | 8/1993 | Barber | |
| 5,336,223 A | 8/1994 | Rogers | |
| 5,360,430 A | 11/1994 | Lin | |
| 5,397,364 A | 3/1995 | Kozak et al. | |
| 5,480,442 A | 1/1996 | Bertagnoli | |
| 5,522,899 A | 6/1996 | Michelson | |
| 5,571,190 A | 11/1996 | Ulrich et al. | |
| 5,571,192 A | 11/1996 | Schönhöffer | |
| 5,658,335 A | 8/1997 | Allen | |
| 5,702,451 A | 12/1997 | Biedermann et al. | |
| 5,702,453 A | 12/1997 | Rabbe et al. | |
| 5,702,455 A | 12/1997 | Saggar | |

(Continued)

FOREIGN PATENT DOCUMENTS

DE    196 22 827 A1    12/1997

(Continued)

OTHER PUBLICATIONS

"International Search Report," International Application No. PCT/US2007/066020, Sep. 26, 2007, European Patent Office, Rijswiijk, Netherlands.

*Primary Examiner* — Eduardo C Robert
*Assistant Examiner* — James Palmer

(57) ABSTRACT

An implant for insertion between vertebral members in which an inner member, intermediate member, and outer member are concentrically disposed. The inner and outer members may comprise end plates to contact the vertebral members. The outer member may include a tapered interior wall. A locking element is movably contained within an opening that extends through a sidewall of the intermediate member. The intermediate member is displaceable longitudinally in first and second directions relative to the outer member. Displacement of the intermediate member in the first direction tends to force the locking element laterally into contact with the inner and outer members. A biasing member may urge the intermediate member in the first direction. Displacement of the intermediate member in the second direction allows the locking element to be laterally displaced out of contact with the inner member.

40 Claims, 8 Drawing Sheets

U.S. PATENT DOCUMENTS

| | | | |
|---|---|---|---|
| 5,723,013 A * | 3/1998 | Jeanson et al. | 623/17.16 |
| 5,725,528 A | 3/1998 | Errico et al. | |
| 5,776,197 A | 7/1998 | Rabbe et al. | |
| 5,776,198 A | 7/1998 | Rabbe et al. | |
| 5,989,290 A | 11/1999 | Biedermann et al. | |
| 6,015,436 A | 1/2000 | Schonhoffer | |
| 6,080,193 A | 6/2000 | Hochshuler et al. | |
| 6,086,613 A | 7/2000 | Camino et al. | |
| 6,156,038 A | 12/2000 | Zucherman et al. | |
| 6,176,881 B1 | 1/2001 | Schär et al. | |
| 6,190,413 B1 | 2/2001 | Sutcliffe | |
| 6,190,414 B1 | 2/2001 | Young et al. | |
| 6,193,755 B1 | 2/2001 | Metz-Stavenhagen et al. | |
| 6,193,756 B1 | 2/2001 | Studer et al. | |
| 6,200,348 B1 | 3/2001 | Biedermann et al. | |
| 6,296,665 B1 | 10/2001 | Strnad et al. | |
| 6,299,644 B1 | 10/2001 | Vanderschot | |
| 6,344,057 B1 | 2/2002 | Rabbe et al. | |
| 6,352,556 B1 | 3/2002 | Kretschmer et al. | |
| 6,375,681 B1 | 4/2002 | Truscott | |
| 6,375,683 B1 | 4/2002 | Crozet et al. | |
| 6,395,034 B1 | 5/2002 | Suddaby | |
| 6,409,766 B1 | 6/2002 | Brett | |
| 6,447,547 B1 | 9/2002 | Michelson | |
| 6,454,806 B1 | 9/2002 | Cohen et al. | |
| 6,520,991 B2 | 2/2003 | Huene | |
| 6,524,341 B2 | 2/2003 | Läng et al. | |
| 6,562,074 B2 | 5/2003 | Gerbec et al. | |
| 6,610,090 B1 | 8/2003 | Böhm et al. | |
| 6,616,695 B1 * | 9/2003 | Crozet et al. | 623/17.11 |
| 6,645,249 B2 | 11/2003 | Ralph et al. | |
| 6,648,917 B2 | 11/2003 | Gerbec et al. | |
| 6,660,038 B2 | 12/2003 | Boyer, II et al. | |
| 6,719,796 B2 | 4/2004 | Cohen et al. | |
| 6,723,126 B1 | 4/2004 | Berry | |
| 6,752,832 B2 | 6/2004 | Neumann | |
| 6,758,862 B2 | 7/2004 | Berry et al. | |
| 6,776,798 B2 | 8/2004 | Camino et al. | |
| 6,783,547 B2 | 8/2004 | Castro | |
| 6,793,678 B2 | 9/2004 | Hawkins | |
| 6,808,538 B2 | 10/2004 | Paponneau | |
| 6,852,129 B2 | 2/2005 | Gerbec et al. | |
| 6,863,673 B2 | 3/2005 | Gerbec et al. | |
| 6,866,682 B1 | 3/2005 | An et al. | |
| 6,908,485 B2 | 6/2005 | Crozet et al. | |
| 7,674,294 B2 * | 3/2010 | Karahalios et al. | 623/17.11 |
| 7,887,594 B2 * | 2/2011 | Berry et al. | 623/17.16 |
| 2003/0191531 A1 | 10/2003 | Berry et al. | |
| 2003/0199980 A1 | 10/2003 | Siedler | |
| 2004/0049271 A1 | 3/2004 | Biedermann et al. | |
| 2004/0073314 A1 | 4/2004 | White et al. | |
| 2004/0172129 A1 | 9/2004 | Schafer et al. | |
| 2004/0181283 A1 | 9/2004 | Boyer, II et al. | |
| 2004/0186569 A1 | 9/2004 | Berry | |
| 2005/0004572 A1 | 1/2005 | Biedermann et al. | |
| 2005/0060036 A1 | 3/2005 | Schultz et al. | |
| 2005/0090898 A1 | 4/2005 | Berry et al. | |
| 2005/0113921 A1 | 5/2005 | An et al. | |

FOREIGN PATENT DOCUMENTS

| | | |
|---|---|---|
| EP | 1 080 703 A2 | 8/2000 |
| EP | 1 188 424 A1 | 8/2001 |
| FR | 2 850 563 A1 | 8/2004 |
| WO | 98/46173 A | 10/1998 |
| WO | 00/23013 A | 4/2000 |
| WO | WO 03/073964 A1 | 9/2003 |
| WO | WO 03/096937 A1 | 11/2003 |
| WO | WO 2004/026157 A2 | 4/2004 |
| WO | WO 2004/096103 A1 | 11/2004 |
| WO | WO 2005/055887 A2 | 6/2005 |

* cited by examiner

EXPANDABLE VERTEBRAL IMPLANT AND METHODS OF USE

BACKGROUND

Spinal implants are often used in the surgical treatment of spinal disorders such as degenerative disc disease, disc herniations, scoliosis or other curvature abnormalities, and fractures. Many different types of treatments are used, including the removal of one or more vertebral bodies and/or intervertebral disc tissue. In some cases, spinal fusion is indicated to inhibit relative motion between vertebral bodies. In other cases, dynamic implants are used to preserve motion between vertebral bodies. In yet other cases, relatively static implants that exhibit some degree of flexibility may be inserted between vertebral bodies.

Regardless of the type of treatment and the type of implant used, surgical implantation tends to be a difficult for several reasons. For instance, access to the affected area may be limited by other anatomy. Further, a surgeon must be mindful of the spinal cord and neighboring nerve system. The size of the implant may present an additional obstacle. In some cases, a surgeon may discover that an implanted device has an inappropriate size for a particular application, which may require removal of the implant and insertion of a different implant. This trial and error approach may increase the opportunity for injury and is certainly time-consuming. Expandable implants are becoming more prevalent as a response to some of these concerns. However, the expansion mechanism in some of these devices tends to be complex and large. In some devices, the expansion mechanism is a ratcheting mechanism that provides limited positional resolution. Consequently, existing devices do not appear to address each of these issues in a manner that improves the ease with which the device may be surgically implanted.

SUMMARY

Illustrative embodiments disclosed herein are directed to an implant for insertion between vertebral members in which an inner member, intermediate member, and outer member are concentrically disposed. Each member may have a circular cross section or asymmetric cross section to maintain relative clocking between the members. The inner and outer members may comprise end plates to contact the vertebral members. The outer member may include a tapered interior wall. A locking element is movably contained within an opening that extends through a sidewall of the intermediate member. In one embodiment, the locking element is a sphere. In one embodiment, the locking element is a cylinder. The intermediate member is displaceable longitudinally in first and second directions relative to the outer member. Displacement of the intermediate member in the first direction tends to force the locking element laterally into contact with the inner and outer members. A biasing member may urge the intermediate member in the first direction. Displacement of the intermediate member in the second direction allows the locking element to be laterally displaced out of contact with the inner member. Moving the inner member in the second direction may expand the implant. Moving the intermediate member in the second direction while moving the inner member in the first direction may compress the implant.

DETAILED DESCRIPTION

Figure 1:
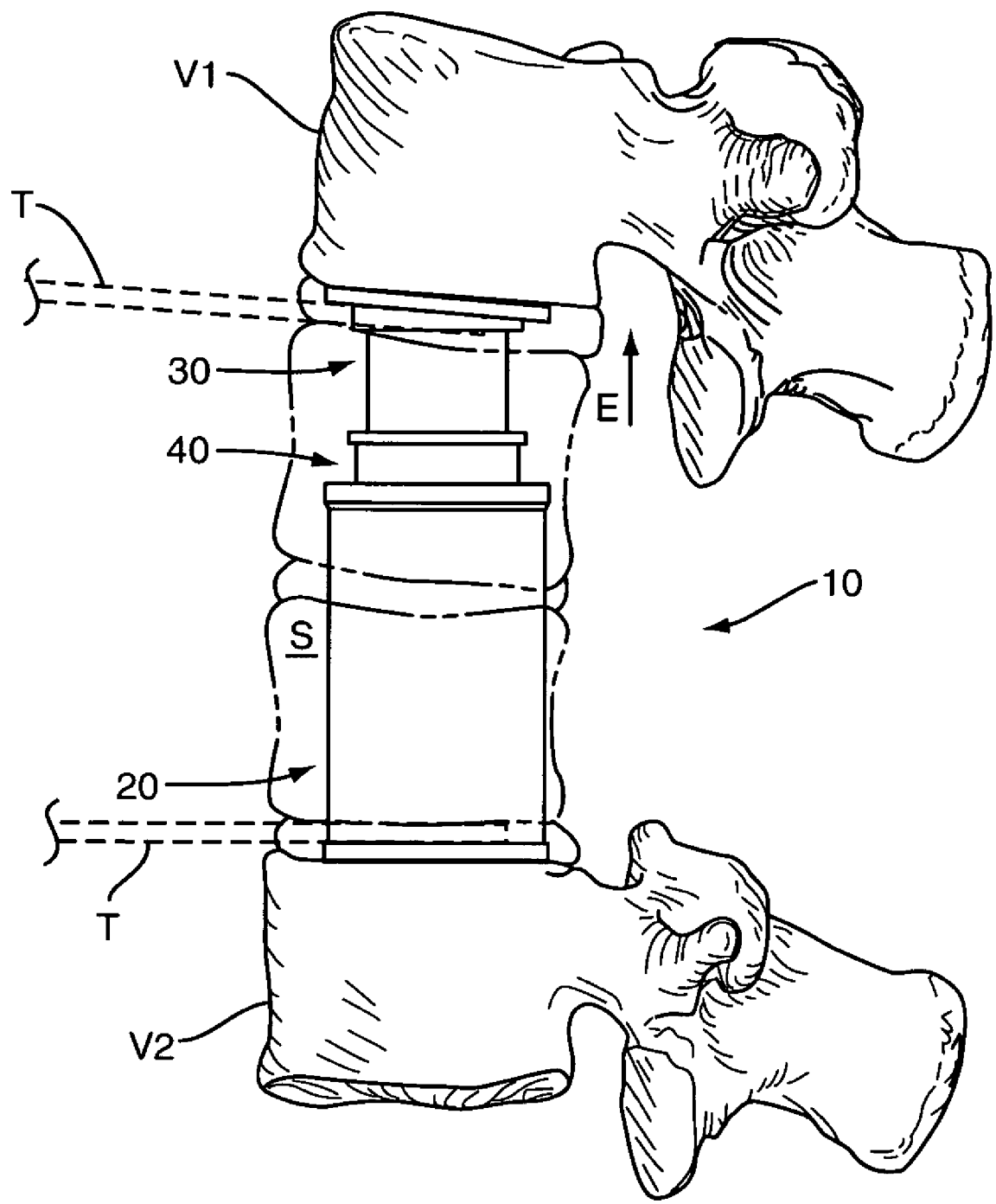
FIG. 1 is a side elevation view of a vertebral implant according to one embodiment positioned between vertebral bodies.

The various embodiments disclosed herein are directed to vertebral implants that are expandable to achieve a desired distraction between vertebral bodies. The vertebral implant includes a locking mechanism that permits infinite adjustability in an expansion direction while restricting motion in an opposite direction. An exemplary implant 10 for supporting vertebral bodies is illustrated in FIG. 1. In one embodiment, the implant 10 is a vertebrectomy implant positionable within an intervertebral space to span one or more vertebral levels along the longitudinal axis of the spinal column. Although the illustrated embodiment of the implant 10 spans two vertebral levels, it should be understood that the implant 10 may be configured to span a single vertebral level or three or more vertebral levels.

Figure 2:
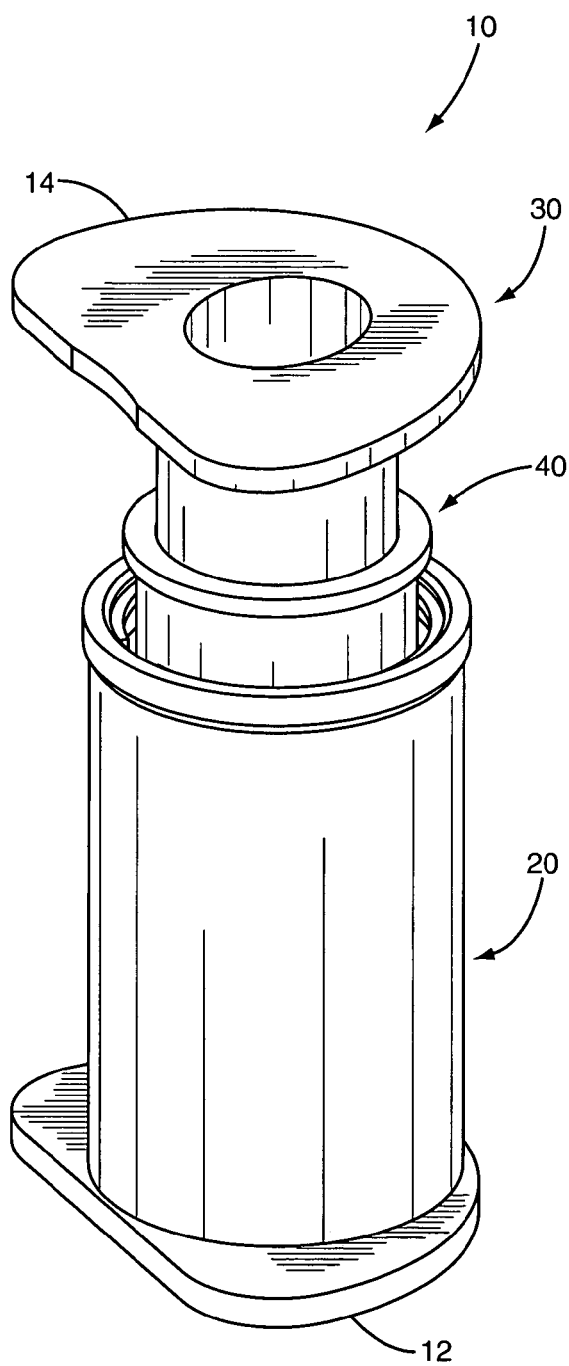
FIG. 2 is a perspective view of one embodiment of a vertebral implant.

A perspective view of the implant 10 is provided in FIG. 2. An exploded assembly view of the implant 10 is provided in FIG. 3. The device 10 comprises a first member 20, a second member 30, and a lock 40. Generally, the first member 20 and second member 30 are expandably coupled to one another. That is, the second member 30 is disposed within the first member 20 and is expandable in the direction of the arrow labeled E in FIG. 1. The lock 40 generally prevents motion of the second member 30 relative to the first member 20 in the substantially opposite direction (i.e., compression). However, as will be explained below, the lock 40 may be released to allow compression. A similar configuration for the lock 40 is disclosed in commonly assigned U.S. patent application Ser. No. 11/335,389, filed Jan. 19, 2006, the relevant portions of which are hereby incorporated by reference herein.

The first member 20 includes a first end member 12 disposed at an end of a first body 16. Similarly, the second member 30 includes a second end member 14 disposed at an end of a second body 18. The end members 12, 14 are adapted to engage the endplates of upper and lower vertebral bodies V1, V2 as shown in FIG. 1. Accordingly, the end members 12, 14 may be shaped and/or sized to match the anatomy of the endplates. The end members 12, 14 may be wider than the respective bodies 16, 18, though this is not explicitly required. As a result of the expandable nature of the implant 10, the end members 12, 14 may be distracted a desired amount to maintain an intervertebral axial space S between the upper and lower vertebral bodies V1, V2 following the removal of one or more vertebral levels (shown in phantom). To facilitate insertion of the implant 10, first and second members 20, 30 may be collapsed relative to each other. Once the implant 10 is inserted between the vertebral bodies V1, V2, the end members 12, 14 may be distracted using a surgical tool T (represented by dashed lines) to maintain the desired intervertebral spacing S.

The implant 10 and its various components may be constructed a variety of biocompatible materials. Some non-limiting examples include non-metallic substances such as, for example, carbon fiber materials, polymers, or copolymers, including varieties made from materials such as PEEK and UHMWPE. In further embodiments, the implant 10 may be formed of metals, such as, for example, stainless steel, titanium, cobalt-chrome, and shape memory alloys.

Figure 3:
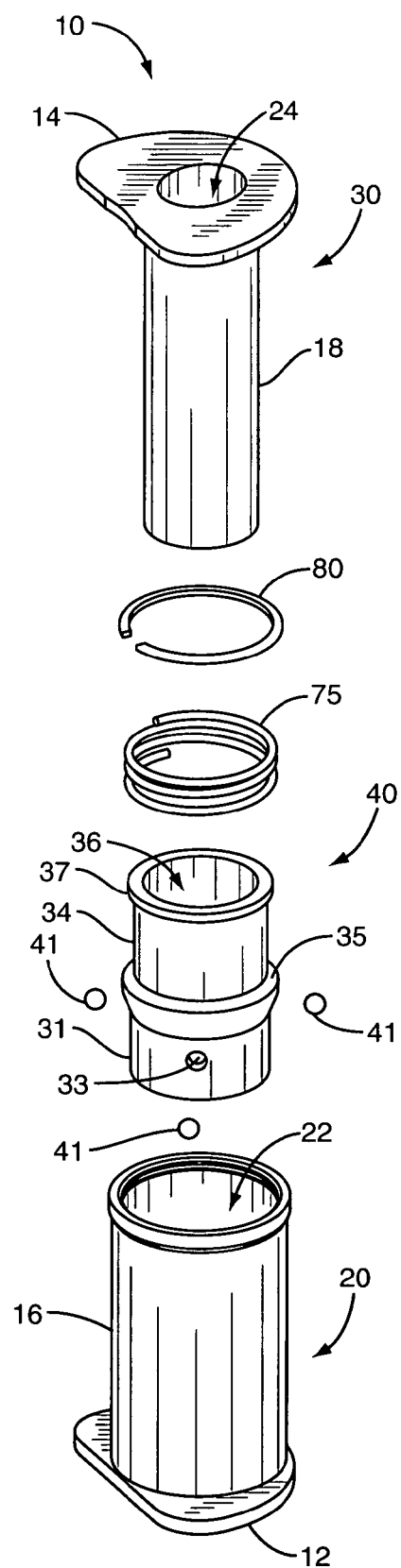
FIG. 3 is an exploded perspective view of one embodiment of a vertebral implant.

The first member 20, in one embodiment, includes a hollow elongated first body 16 having an open interior 22 that extends through the length. Similarly, the second member 30 includes a hollow elongated second body 18 having an open interior 22 that extends through the length. The open interior of the first member 20 and second member 30 provides a cavity in which bone growth promoting materials such as bone grafts or BMP may be inserted. Alternatively, the second body 18 may be solid. One embodiment of the lock 40 includes a lock body 31 having one or more openings 33 in a lower section. One embodiment of the lock 40 includes one or more locking elements 41 that fit within the openings 33. Locking elements 41 may move within the openings 33 between the locked and unlocked positions. FIG. 3 also shows a retainer 80 and biasing member 75 that cooperate to retain the lock body 31 within the open interior 22 of the first member 20. As described below, the biasing member 75 may also maintain the locking elements 41 in the locked position.

Figure 4:
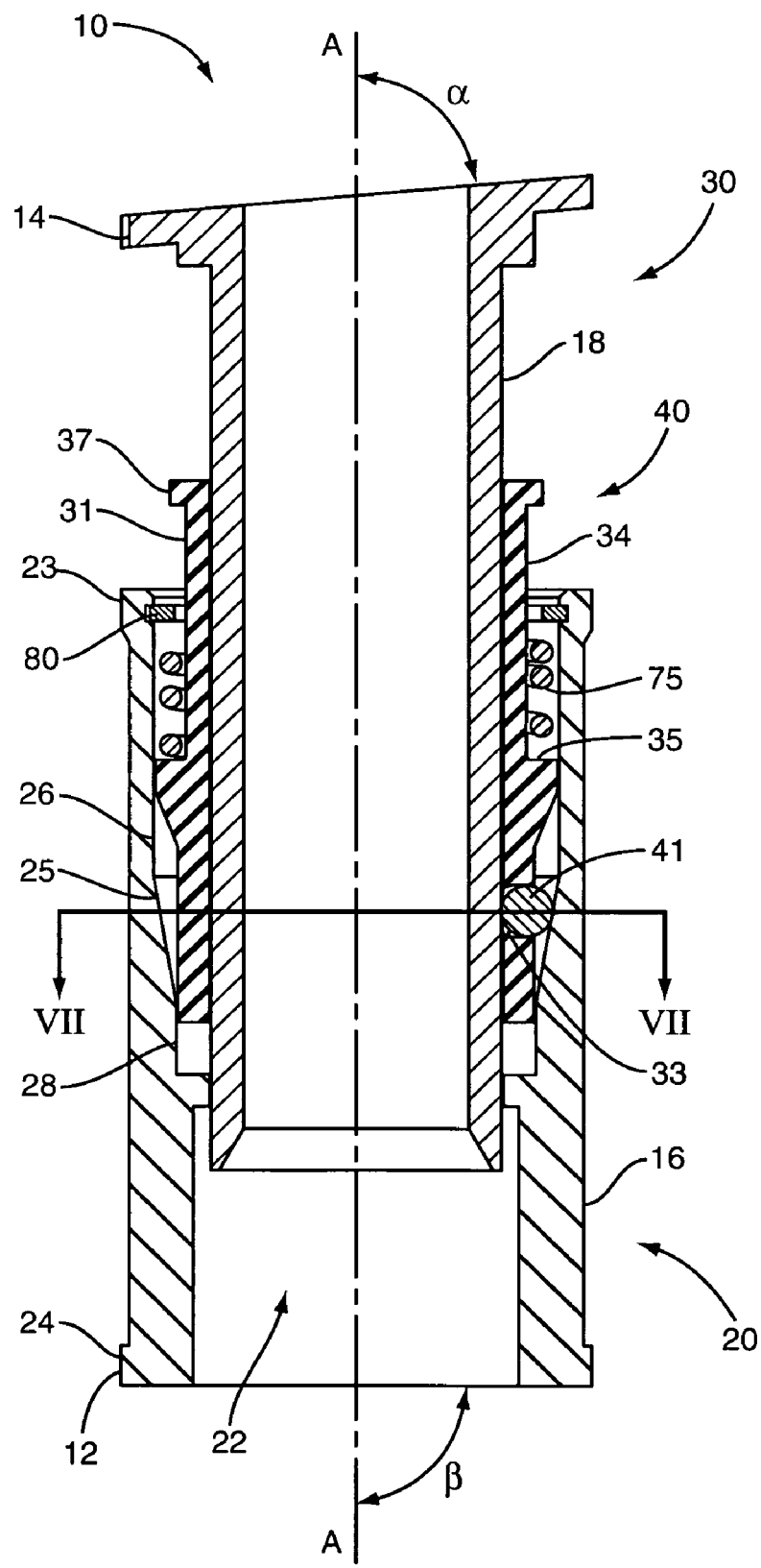
FIG. 4 is a longitudinal cross section view of a vertebral implant according to one embodiment depicted in a locked state.

FIG. 4 illustrates a longitudinal cross section of one embodiment of the implant 10. In this embodiment, the first body 16 includes an elongated length extending between a first end 23 and a second end 24. In another embodiment, first body 16 includes a shorter length extending around the second body 18 of the second member 30. For example, in certain applications, the implant 10 may be used in disc replacement surgery or for the replacement of a single vertebral level. In these cases, a shortened body 16 may be appropriate. The first body 16 may be hollow forming the interior section 22 that extends the length. In one embodiment, first body 16 includes a substantially circular cross-sectional shape with the interior section 22 also being substantially circular. In other embodiments, first body 16 and the interior section 22 include non-circular cross-sectional shapes. Generally, for either configuration, the first body 16, lock body 31, and second body 18 may be concentric. The interior section 22 tapers from a first width at wall 26 disposed towards the first end 23 to a second, narrower width at wall 28 disposed towards the second end 24. A tapered wall 25 is disposed therebetween and provides a transition between the different widths.

In one embodiment, the lock 40 includes lock body 31 sized to fit within the interior section 22. In one embodiment, a limited section of the second member 30 fits within the interior section 22. In one embodiment as illustrated in FIG. 3, lock body 31 includes an interior section 36 that extends the length and is sized to receive the second body 18. One or more openings 33 may extend through the lock body 31 and each is sized to receive a locking element 41. Openings 33 may be positioned along the length of the lock body 31 at a variety of locations. In one embodiment as illustrated in FIG. 4, openings 33 are positioned at a lower section of the lock body 31 to interact with the tapered wall 25 of the first body 16 as will be explained in detail below. In one embodiment, a single opening 33 is positioned within the lock body 31. In one embodiment, the lock body 31 includes three openings 33 that are aligned within a common plane and spaced about 120 degrees apart around the lock body 31.

One embodiment of the lock body 31 further includes a neck section 34 with a reduced width that is spaced inward from the inner sidewalls of first body 16. A shelf 35 having a larger width is positioned at one end of the neck section 34 in one embodiment. A cap 37 including a larger width may be positioned at an upper end of the lock body 31.

In one embodiment, the lock 40 includes one or more locking elements 41 movably positioned at the openings 33. In one embodiment, locking elements 41 comprise spherical balls, such as ball bearings. In another embodiment, locking elements 41 include other shapes. For example, in one embodiment described below, the locking element 41 includes a substantially cylindrical shape. In embodiments having plural locking elements 41, each of the elements 41 may include the same or different shapes and sizes. In one embodiment, each locking element 41 travels back and forth relative to the opening 33. As illustrated in the embodiment of FIG. 4, a thickness of the locking element 41 is greater than a thickness of the lock body 31 forming the opening 33 (other sections of the lock body 31 may include a greater thickness than the locking element). Therefore, downward movement of the lock body 31 relative to the first member 20 causes the locking elements 41 to move radially inward when sliding along the tapered wall 25. It is worth noting that in FIG. 4, the implant 10 is depicted with the lock 40 in the locked position.

Figure 5:
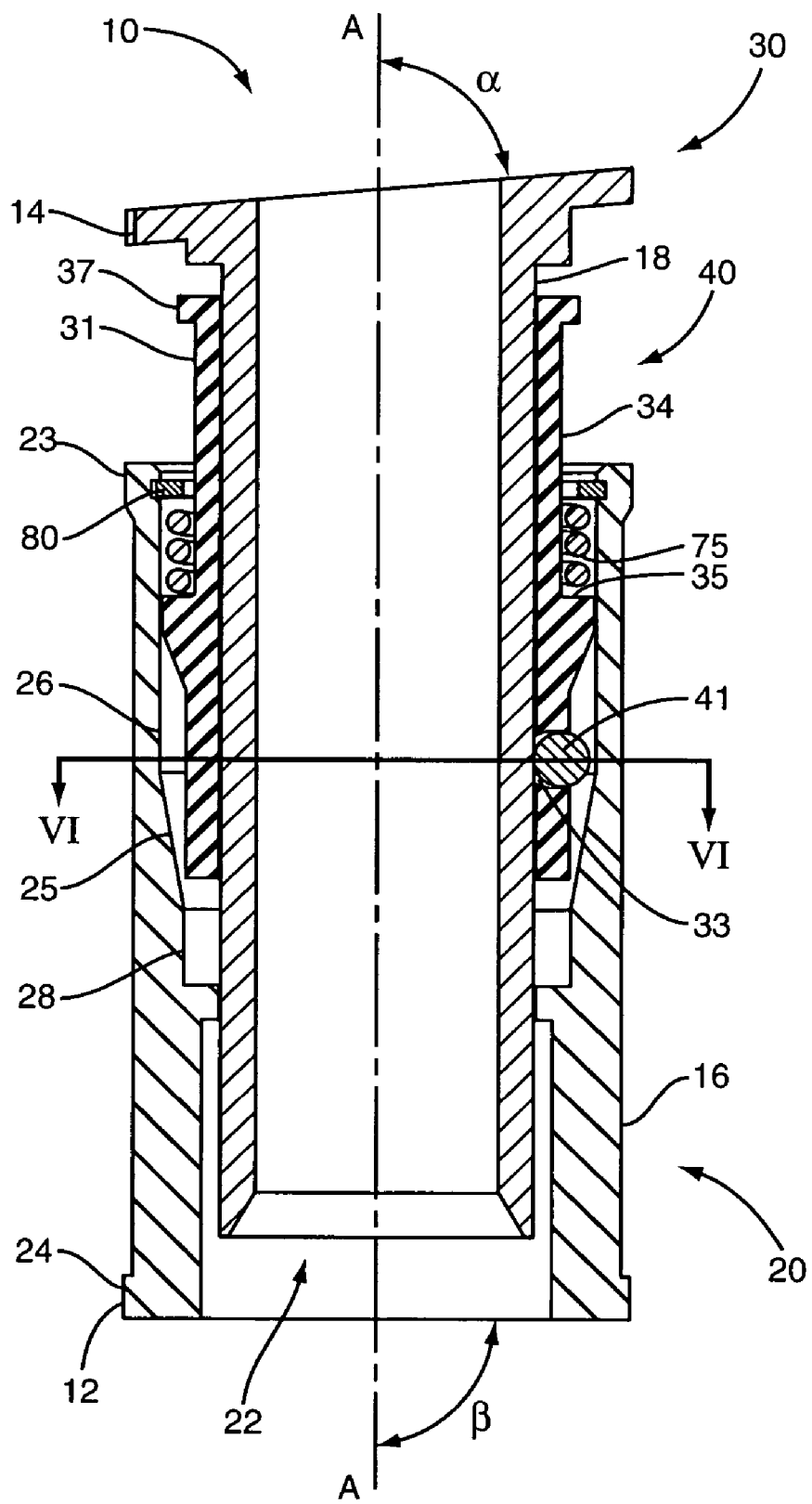
FIG. 5 is a longitudinal cross section view of a vertebral implant according to one embodiment depicted in an unlocked state.

FIG. 5 illustrates one embodiment in the unlocked position. In this embodiment, second member 30 extends through the hollow interiors 22, 36 of the first member 20 and lock body 31. In one embodiment, second member 30 is aligned with a centerline of a longitudinal axis A that extends through the second body 18 of first member 20 and lock body 31 of lock 40. The lock body 31 is positioned within the first member 20 with the opening 33 positioned at wall 26 where the interior section 22 includes a wider first width. In one embodiment, a space formed between second body 18 of the second member 30 and the sidewall 26 of the interior section 22 is greater than the thickness of the locking elements 41 allowing the locking elements 41 to freely move thus preventing binding with the second member 30.

Figure 6:
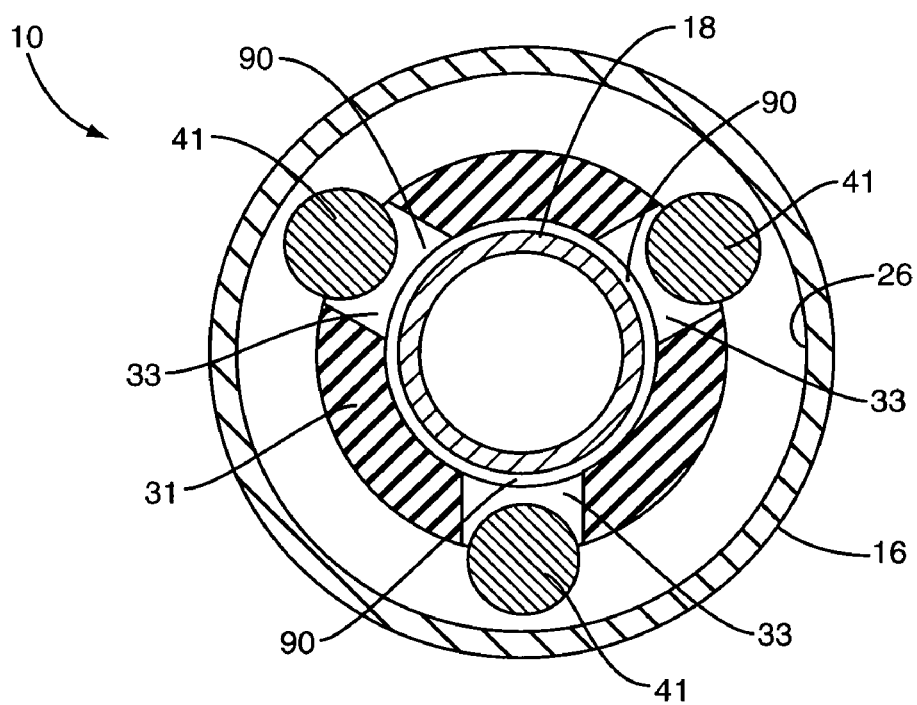
FIG. 6 is an axial cross section view according to the section lines VI-VI in FIG. 5.

FIG. 6 is a cross-sectional view of the device of FIG. 5 cut along the section line VI-VI. In this embodiment, space 90 formed between the second body 18 and the interior sidewall 26 of the first body 16 is greater than the thickness of the locking elements 41. Thus, the locking elements 41 may move within the space 90 and the second member 30 may move axially relative to the first member 20, including in compression.

Figure 7:
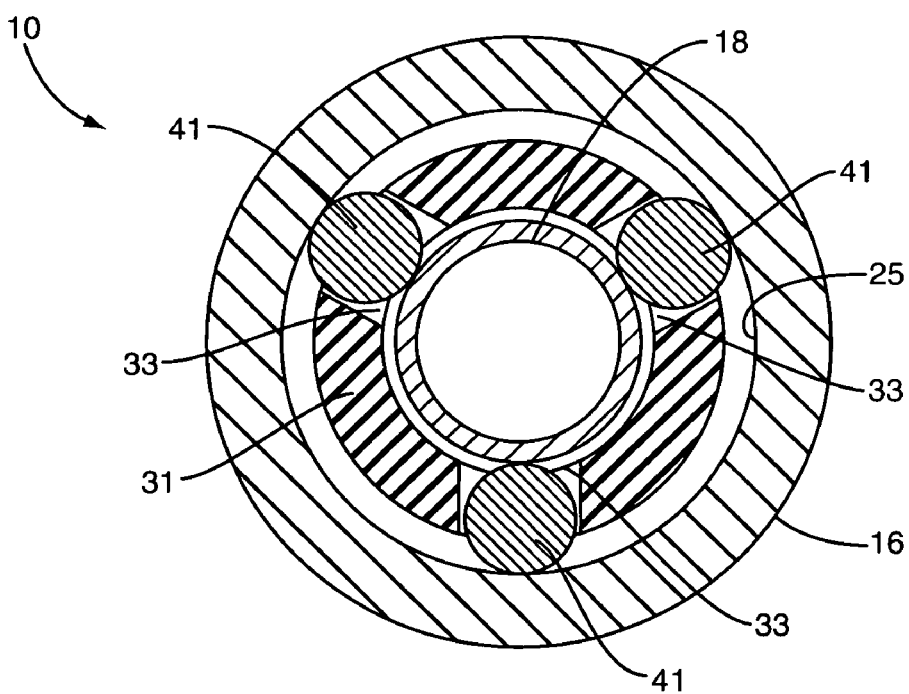
FIG. 7 is an axial cross section view according to the section lines VII-VII in FIG. 4.

FIGS. 4 and 7 illustrate one embodiment of an implant 10 in the locked position. In this configuration, the lock body 31 is moved downward within the first body 16. Openings 33 are now aligned at tapered wall 25 where the space 90 formed between the second body 18 and the first body 16 is less than the thickness of the locking elements 41. This causes the locking elements 41 to deflect inward through the openings 33 and into contact with second body 18. In one embodiment, this contact locks the second member 30 to the first member 20 and prevents compression.

However, due to the orientation of the tapered wall 25, the second member 30 may still extend relative to the first member 20. Furthermore, the tapered wall 25 produces a decreasing width of the interior section 22 in the compression direction. The decreasing width creates greater interference to prevent compression of the implant 10. Therefore, the locking elements 41 may apply a greater force on the second member 30 the further the second wall 18 and lock body 31 are inserted downward into the first member 20.

In one embodiment, a biasing mechanism 75 is positioned between the first member 20 and lock 40. In one embodiment, a first end of the biasing mechanism 75 contacts the shelf 35 of the lock body 31. In one embodiment, a retainer 80 attached to the inner wall of the first body 16 forms a contact surface for a second end of the biasing mechanism 75. The biasing mechanism 75 in one embodiment includes a cylindrical configuration that is disposed around the neck 34. In one specific embodiment, biasing mechanism 75 is a coil spring. In one embodiment, biasing mechanism 75 applies a force on the lock body 31 to maintain the lock 40 towards the locked position. The force may be adequate to lock the implant 10 against compression between the first member 20 and second member 30. Unlocking the implant 10 may require moving the lock body 31 away from the first member 20. Unlocking the implant 10 may require moving the lock body 31 against the biasing force applied by the biasing mechanism 75. In one embodiment, grasping and pulling the cap 37 towards the second end member 14 will unlock the lock 40. Unlocking the implant 10 may require moving the lock body 31 upward to a point where the recesses 33 are positioned in a region of the interior section 22 having a larger interior width.

Figure 8:
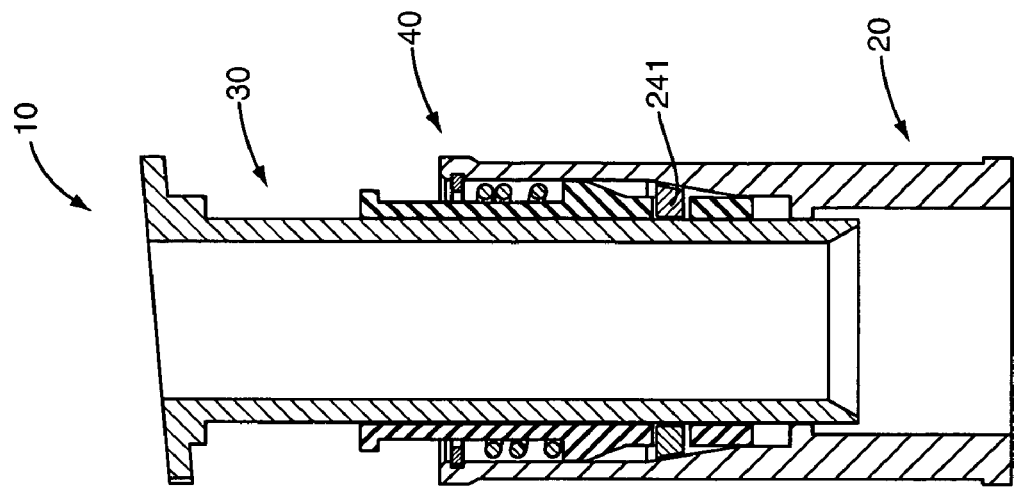
FIG. 8 is a longitudinal cross section view of a vertebral implant according to one embodiment.

Locking elements 41 may further include a variety of shapes and sizes. Embodiments as illustrated in FIGS. 3-7 incorporate a locking element 41 including a spherical shape that moves within the openings 33. Another embodiment such as that illustrated in FIG. 8 incorporates a locking element 141 that includes a different shape. In one embodiment, locking element 141 is contained within an opening 33 within the lock body 31. In another embodiment as illustrated in FIG. 8, locking element 141 is positioned outside of the lock body 31 and at a position to be contacted by the lock body 31. Locking element 141 may be operatively connected to the lock body 31, or may be unconnected.

Figure 9:
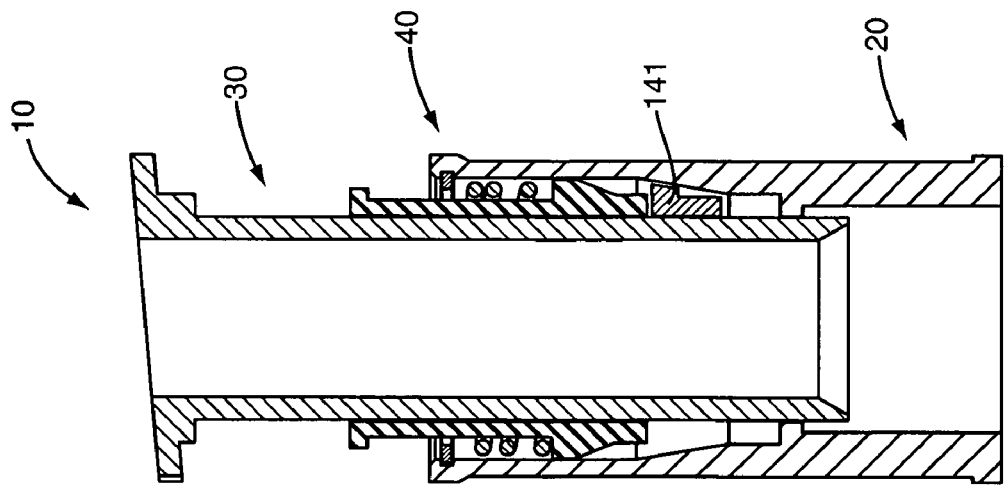
FIG. 9 is a longitudinal cross section view of a vertebral implant according to one embodiment.

The number of locking elements 41 may vary depending upon the application. Certain embodiments feature multiple locking elements 41. For embodiments with multiple locking elements 41, the elements 41 may be positioned within the same plane relative to the lock body 31. In other embodiments, two or more of the locking elements 41 may be positioned within different planes. In one embodiment, a single locking element 41 locks the device 10. For example, FIG. 9 depicts an embodiment in which a single, ring shaped locking element 241 is used. The ring shaped locking element 241 may be split to allow radial compression of the locking element 241 or form a continuous ring to resist radial compression.

The end members 12, 14 may be disposed at various angles relative to a longitudinal axis of the implant 10. The orientation of the end members 12, 14 may be varied to accommodate a desired angle between vertebral bodies (e.g., to achieve desired lordotic or kyphotic curvatures). For instance, FIG. 4 shows angles α and β respectively describing the angle between end members 12, 14 and longitudinal axis A. In one embodiment, angles α and β may be substantially 90 degrees, which implies that the end members 12, 14 are substantially parallel. In other embodiments, the end members 12, 14 may be parallel but disposed at some acute or obtuse angle relative the axis A. In other embodiments the end members 12, 14 may be disposed at different angles α and β relative to axis A.

Figure 10:
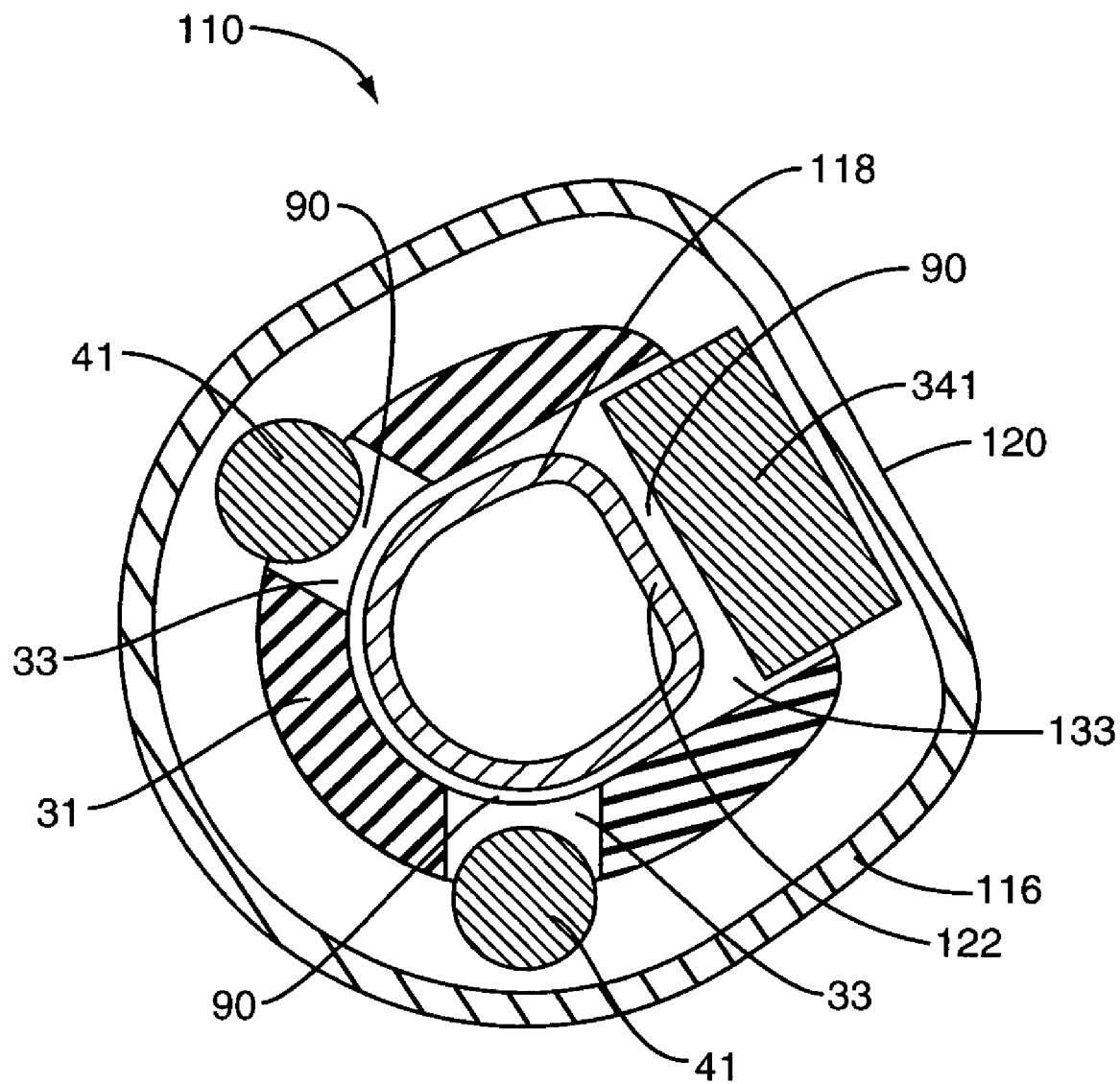
FIG. 10 is an axial cross section view of a vertebral implant according to one embodiment.

It may be desirable to maintain the angles α and β aligned about a common anatomic plane. For instance, a surgeon may wish to orient the angles α and β within a sagittal or coronal plane. Further, it may be desirable to maintain the angles α and β at some relative clocking position (including aligned or misaligned) relative to each other. Accordingly, in one embodiment shown in FIG. 10, the bodies 116, 118 of the first member 20 and second member 30 are asymmetric or non-cylindrical. In the illustrated embodiment, the first body 116 and the second body 118 are substantially D-shaped with each having a single flat sidewall 120, 122. The flat sidewalls 120, 122 maintain a keyed or clocked relationship between the first member 20 and second member 30. In other embodiments, the first body 116, and second body 118 may include additional flat surfaces. For example, the first and second bodies 116, 118 may be substantially triangular, square, or polygonal. Other asymmetric configurations that do not have flat sidewalls 120, 122 may be used. For example, both bodies 116, 118 may include an elliptical cross section. A non-spherical locking element 141 may be used at the interface between the flat sidewalls 120, 122. In one embodiment, the locking element 141 is cylindrical as depicted in FIG. 10.

Figure 11:
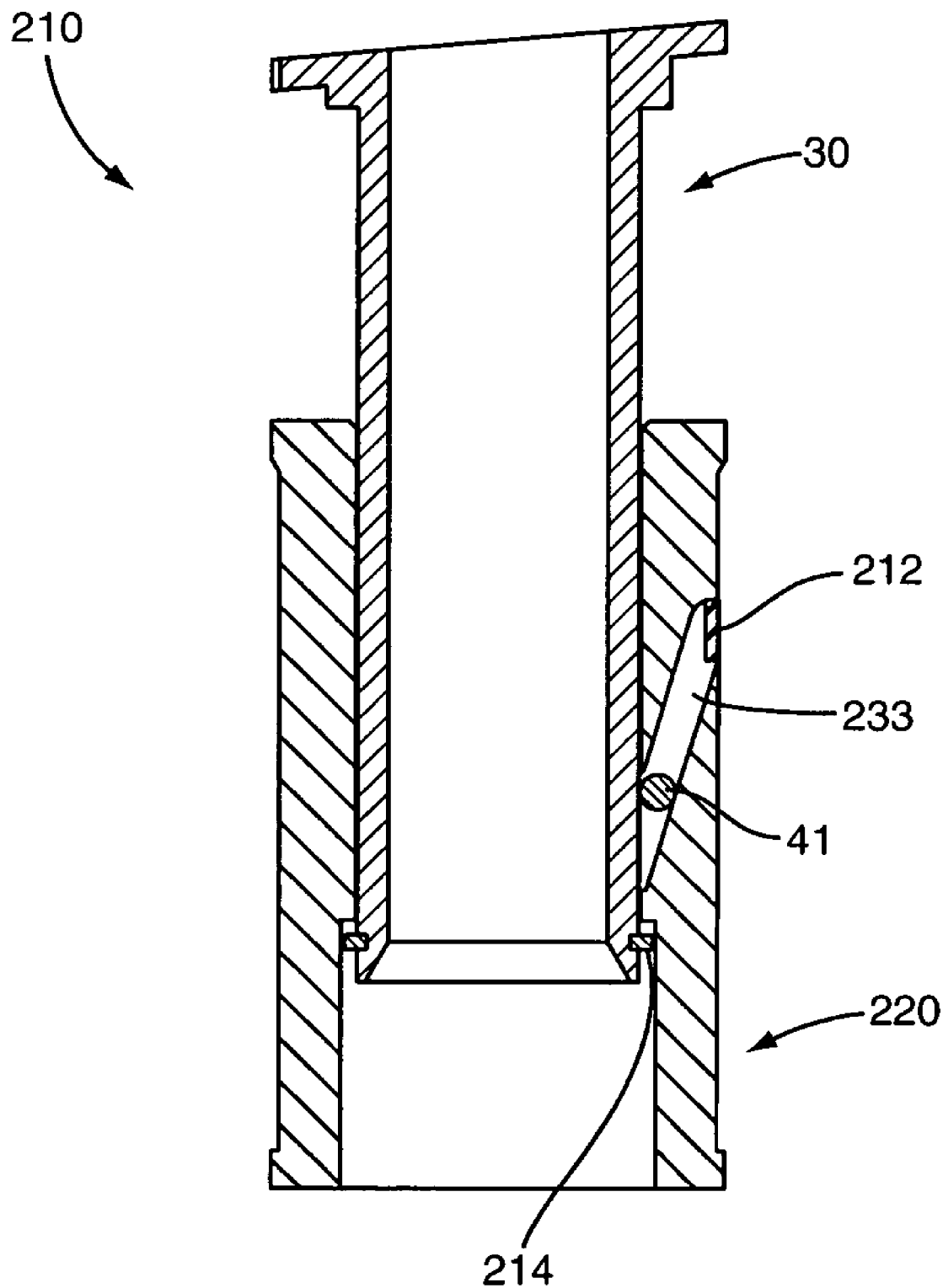
FIG. 11 is a longitudinal cross section view of a vertebral implant according to one embodiment.

Embodiments above have incorporated a lock body 31 as part of the lock 40. The lock body 31 offers several advantages, including but not limited to providing a recess 33 in which the locking elements 41 are retained as well as providing a release mechanism by which the first member 20 and second member 30 may be compressed. Nevertheless, it is certainly possible to incorporate the locking elements 41 in the implant 10 without the use of a separate lock body 31. For example, in an embodiment shown in FIG. 11, the implant 210 includes a first member 220, a second member 30, and locking element 41. More than one locking element 41 may be distributed radially about the implant 210. In the illustrated embodiment, the first member 220 includes an opening 233 extending through a sidewall of the implant in which the locking element 41 is positioned. A comparable configuration may be arranged where the locking elements 41 are retained in openings in the second member 30. In contrast with previous embodiments, the opening 233 is slanted in a way that permits extension of the second member 30 relative to the first member 220. However, the slanted orientation of the opening 233 creates greater interference as second member 30 is compressed relative to the first member 20. In fact, the locking elements 41 may apply a greater force on the second member 30 the further the second member 30 is inserted downward into the first member 220. If desired, a retainers 212, 214 may be included to keep the second member 30 within the first member 220 and further to keep the locking element 41 in the opening 233.

The various Figures and embodiments disclosed herein have depicted spinal implant devices that are inserted between or adjacent vertebral bodies. However, the teachings disclosed are certainly applicable to other types of spinal implant devices, including interspinous spacers, rods, and other implants that are coupled to vertebrae V1, V2.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, the embodiments disclosed herein have contemplated a single implant positioned between vertebral bodies V1, V2. In other embodiments, two or more smaller implants may be inserted between the vertebral bodies V1, V2. The present embodiments are, therefore, to be considered in all respects as illustrative and not restrictive, and all changes coming within the meaning and equivalency range of the appended claims are intended to be embraced therein.

What is claimed is:

1. An implant for insertion between vertebral members in a patient comprising:
    an outer member including a first end to contact a first of the vertebral members;
    an inner member including a second end to contact a second of the vertebral members;
    an intermediate member disposed so as to overlap within the outer member and the inner member at a common position along a longitudinal axis of the implant to form a three-layer arrangement, the intermediate member being displaceable longitudinally in first and second directions relative to the outer member, the intermediate member further having a longitudinal channel to contain the inner member and a lateral opening that extends through the intermediate member into the channel; and
    a locking element disposed at least partly within the lateral opening and movable with respect thereto, the locking element being positioned within an interior of the outer member;
    displacement of the intermediate member in the first direction forces the locking element inward toward the inner member;
    displacement of the intermediate member in the second direction allows the locking element to be outwardly displaced away from the inner member.

2. The implant of claim 1, wherein the locking element includes a diameter that is greater than a width of the lateral opening.

3. The implant of claim 2 wherein the locking element includes a spherical shape.

4. The implant of claim 2 wherein the locking element includes a cylindrical shape.

5. The implant of claim 1, wherein a section of the intermediate member is disposed outside of the outer member.

6. The implant of claim 1, wherein the outer member includes a tapered inner wall with displacement of the intermediate member in the first direction moving the locking element into a narrowed section of the outer member and displacement in the second direction moving the locking element into an enlarged section of the outer member.

7. The implant of claim 1, wherein the opening is substantially perpendicular to the channel.

8. The implant of claim 1, wherein the outer, intermediate, and inner members each include a cylindrical body.

9. The implant of claim 1, wherein the outer, intermediate, and inner members each include an asymmetric cross section within a plane substantially perpendicular to the longitudinal axis of the implant.

10. The implant of claim 1 wherein the first end is oriented at a first angle relative to the longitudinal axis of the implant.

11. The implant of claim 1 wherein the second end is oriented at a second angle relative to the longitudinal axis of the implant.

12. An implant for insertion between vertebral members in a patient comprising:
    a first member including a first end to contact a first of the vertebral members;
    a second member concentrically coupled to the first member and including a second end to contact a second of the vertebral members; and
    a sphere movably contained within the implant, positioned fully between the first end and an opposite end of the first member, and disposed in contact with the second member and a tapered surface of the first member;
    the second member being displaceable longitudinally in first and second directions relative to the first member with displacement of the second member in the first direction forcing the sphere to move relative to the tapered surface to provide a clearance between the first member, the second member, and the sphere, and
    displacement of the second member in the second direction forcing the sphere to move relative to the tapered surface to create an interference between the first member, the second member, and the sphere.

13. The implant of claim 12, wherein the second member is at least partially disposed within the first member.

14. The implant of claim 12, wherein the first and second members each include an asymmetric cross section within a plane substantially perpendicular to the first and second directions.

15. The implant of claim 12, further comprising a third member sized to fit at least partially within the first member, the sphere disposed in an opening in the third member that extends through a sidewall of the third member.

16. The implant of claim 15, wherein the third member is displaceable longitudinally in the first and the second directions, displacement of the third member in the first direction allows the sphere to be displaced out of contact with the second member, and displacement of the third member in the second direction forcing the sphere laterally into contact with the second member.

17. The implant of claim 12, wherein the tapered surface is disposed at an interior wall of the first member.

18. The implant of claim 12, wherein the tapered surface is formed by a slanted opening in the first member that extends through a sidewall of the first member.

19. An implant for insertion between vertebral members in a patient comprising:
    a first member including a first end to contact a first of the vertebral members, the first member including an interior section formed by a sidewall, the interior section having a tapered portion that extends between a first level having a first width and a second level having a reduced second width;
    a second member movably disposed within the interior section and having a channel;
    a third member including a second end to contact a second of the vertebral members, the third member movably disposed within the channel;
    a locking element sized to move within an opening in the second member, the locking element having a width greater than the opening, the locking element positioned at a longitudinal location where each of the first, second, and third members overlap;
    the second member movable relative to the first member between an unlocked position with the opening positioned in proximity to the first level with the locking element freely movable within the opening, and a locked position with the opening positioned in proximity to the second level with the locking element being forced into contact with the sidewall and the third member.

20. The implant of claim 19, further comprising a biasing member operatively connected to the first member to maintain the second member positioned within the interior section of the first member.

21. The implant of claim 19, further comprising a biasing member operatively connected to the first member to bias the second member towards the locked position.

22. The implant of claim 19, further comprising a second locking element positioned within a second opening in the second member, the second locking element positioned in a common vertical plane with the locking element.

23. The implant of claim 19, wherein the locking element includes a spherical shape.

24. The implant of claim 19, wherein the locking element includes a cylindrical shape.

25. The implant of claim 19, wherein a portion of the second member extends outward from the first member in both the locked and unlocked positions.

26. The implant of claim 19, wherein the first, second, and third members each include a cylindrical body.

27. The implant of claim 19, wherein the first, second, and third members each include an asymmetric cross section within a plane substantially perpendicular to a longitudinal axis.

28. An implant for insertion between vertebral members in a patient comprising:
an outer member including a first end to contact a first of the vertebral members and a tapered inner diameter;
an inner member including a second end to contact a second of the vertebral members, each of the inner and outer members including a cross section shape with a linear sidewall, the cross section shapes each being normal to a longitudinal axis of the implant;
an intermediate member disposed at least partially within the outer member and around the inner member with each of the members being aligned along the longitudinal axis;
a locking element disposed at least partly within an opening within the intermediate member and movable with respect thereto, the locking element including a flattened shape that is complementary to the linear sidewalls;
the intermediate member being displaceable along the longitudinal axis in first and second directions relative to the outer member, displacement of the intermediate member in the first direction forces the locking element against the tapered inner diameter of the outer member and radially inward toward the inner member, displacement of the intermediate member in the second direction allows the locking element to be outwardly displaced away from the inner member.

29. The implant of claim 28, wherein the locking element includes a cylindrical shape with first and second substantially straight sides.

30. The implant of claim 28, wherein cross section shapes of the inner and outer members are substantially D-shaped.

31. The implant of claim 28, wherein cross section shapes of the inner and outer members are substantially polygonal.

32. The implant of claim 28, further comprising a second locking element positioned at least partly within a second opening in the intermediate member.

33. The implant of claim 28, wherein the intermediate member includes a cross section shape that is substantially similar to the inner and outer members.

34. An implant for insertion between vertebral members in a patient comprising:
a first cylindrical member including a first end to contact a first of the vertebral members and including a tapered inner diameter;
a second cylindrical member concentrically coupled to the first cylindrical member and including a second end to contact a second of the vertebral members, each of the first and second cylindrical members including a cross section shape with a linear section, the cross section shapes being normal to a longitudinal axis of the implant; and
a locking element movably contained between the first and second cylindrical members and positioned to contact the linear sections of the first and second cylindrical members;
the second cylindrical member being displaceable longitudinally in first and second directions relative to the first cylindrical member with displacement of the second cylindrical member in the first direction forcing the locking element to contact a reduced section of the tapered inner diameter of the first cylindrical member to create an interference between the first cylindrical member, the second cylindrical member, and the locking element, and
displacement of the second cylindrical member in the second direction positions the locking element at an enlarged section of the tapered inner diameter of the first cylindrical member to provide a clearance between the first cylindrical member, the second cylindrical member, and the locking element.

35. The implant of claim 34, wherein the cylindrical second member is at least partially disposed within the first cylindrical member.

36. The implant of claim 34, wherein the locking element is substantially cylindrical.

37. The implant of claim 34, wherein the cross section shape of the first and second cylindrical members is substantially D-shaped.

38. The implant of claim 34, wherein the cross section shape of the first and second cylindrical members is substantially rectangular.

39. The implant of claim 34, wherein the cross section shape of the first and second cylindrical members is substantially triangular.

40. The implant of claim 34, wherein the cross section shape of the first and second cylindrical members is substantially polygonal.

* * * * *